US010208054B2

(12) United States Patent
Archer et al.

(10) Patent No.: US 10,208,054 B2
(45) Date of Patent: Feb. 19, 2019

(54) METHOD OF PREPARING BUPRENORPHINE

(71) Applicant: Johnson Matthey Public Limited Company, London (GB)

(72) Inventors: Nicolas Archer, Edinburgh (GB); David August, Edinburgh (GB); Michael Bease, Edinburgh (GB); Barbara Jamieson, Edinburgh (GB); Robert S. Marmor, Woodstown, NJ (US)

(73) Assignee: Johnson Matthey Public Limited Company, London (GB)

( * ) Notice: Subject to any disclaimer, the term of this patent is extended or adjusted under 35 U.S.C. 154(b) by 0 days.

(21) Appl. No.: 15/489,146

(22) Filed: Apr. 17, 2017

(65) Prior Publication Data

US 2017/0217978 A1 Aug. 3, 2017

Related U.S. Application Data

(62) Division of application No. 14/349,213, filed as application No. PCT/GB2012/052423 on Oct. 1, 2012, now Pat. No. 9,624,231.

(60) Provisional application No. 61/542,491, filed on Oct. 3, 2011.

(51) Int. Cl.
*C07D 489/12* (2006.01)
*C07D 489/02* (2006.01)
*C07D 489/08* (2006.01)

(52) U.S. Cl.
CPC ......... *C07D 489/02* (2013.01); *C07D 489/08* (2013.01); *C07D 489/12* (2013.01)

(58) Field of Classification Search
CPC .................................................. C07D 489/12
USPC .......................................................... 546/39
See application file for complete search history.

(56) References Cited

U.S. PATENT DOCUMENTS

| 3,474,101 | A | 10/1969 | Bentley |
| 8,227,608 | B2 * | 7/2012 | Allen ................... C07D 489/12 546/38 |
| 8,232,397 | B2 | 7/2012 | Allen et al. |
| 8,962,841 | B2 | 2/2015 | Hudlicky et al. |
| 2009/0005563 | A1 | 1/2009 | Carroll et al. |
| 2010/0087647 | A1 | 4/2010 | Allen et al. |

FOREIGN PATENT DOCUMENTS

| FR | 2554816 A1 | 5/1985 |
| GB | 2313596 | 12/1997 |
| WO | WO-2008070462 A2 | 6/2008 |
| WO | WO-2009067275 A1 | 5/2009 |
| WO | WO-2009122436 A2 | 10/2009 |
| WO | WO-2009132313 A2 | 10/2009 |
| WO | WO-2010039220 A1 | 4/2010 |
| WO | 2013007986 A1 | 1/2013 |

OTHER PUBLICATIONS

Cami-Kobeci et al., "Structural Determinants of Opioid and NOP Receptor Activity in Derivatives of Buprenorphine", Journal of Medicinal Chemistry, 2011, vol. 54, No. 19, pp. 6531-6537.
Coop et al., "Structural Determinants of Opioid Activity in the Orvinols and Related Structures: Ethers of Orvinol and Isoorvinol", Journal of Medicinal Chemistry, 2000, 43, pp. 1852-1857.
Huang et al., "A Facile Synthesis and Structural Verification of Etorphine and Dihydroetorphine from Codeine", Journal of the Chinese Chemical Society, 2011, vol. 58, No. 1 pp. 101-107.
Shutz et al., "Synthesis and Pharmacological Evaluation of 18,19-Dehydrobuprenorphine", Heterocycles, vol. 54, No. 2, 2001, pp. 989-998.
Wu et al., "Functionalization of the 6,15-bridge of the Orvinols. Part 3: Preparation and Pharmacological Evaluation of 18- and 19-hydroxyl Substituted Orvinols", Bioorganic & Medicinal Chemistry Letters 17 (2007) pp. 4829-4831.
Knipmeyer et al, "Analgesics of the 6,14-ethenomorphinan type. 6-Deoxy-7a-orivinols and 6-deoxy-8a-orivinols", J. Med. Chem., 1985, 461-466, 28.
Machara et al, "Improved synthesis of buprenorphine from thebaine and/or oripavine via palladium-catalyzed N-demethylalion/acylation and/or concomitant O-demethylation", Adv. Synth. Catal., 2012, 613-626, 354.
Michne, "2,6-Methano-3-benzazocine-11-propanols. Lack of antagonism between optical antipodes and observation of potent narcotic antagonism by two N-methyl derivatives", J. Med. Chem., 1978, 1322-1324, 21(12).

* cited by examiner

*Primary Examiner* — Charanjit Aulakh
(74) *Attorney, Agent, or Firm* — Shanay M. McCastle

(57) ABSTRACT

An improved process for preparing buprenorphine and a method for increasing the yield of buprenorphine or a derivative thereof.

7 Claims, No Drawings

METHOD OF PREPARING BUPRENORPHINE

CROSS-REFERENCE TO RELATED APPLICATIONS

This application is a divisional of U.S. patent application Ser. No. 14/349,213, filed Apr. 2, 2014, and claims priority benefit of PCT Patent Application No. PCT/GB2012/0542423, filed Oct. 1, 2012 and U.S. Provisional Patent Application No. 61/542,491, filed Oct. 3, 2011, the disclosures of which are incorporated herein by reference in their entireties for all purposes.

FIELD OF THE INVENTION

The present invention provides a process for the production of opiate alkaloids. In particular, the present invention provides an improved process for the production of buprenorphine or a derivative of buprenorphine that increases overall yield and reduces impurities.

BACKGROUND OF THE INVENTION

Buprenorphine is a semisynthetic opiate used medicinally as a powerful analgesic, indicated for the treatment of moderate to severe pain and opioid dependence. The preparation of buprenorphine from thebaine is known and has been reported in publications to be carried out by the following 6 major step scheme:

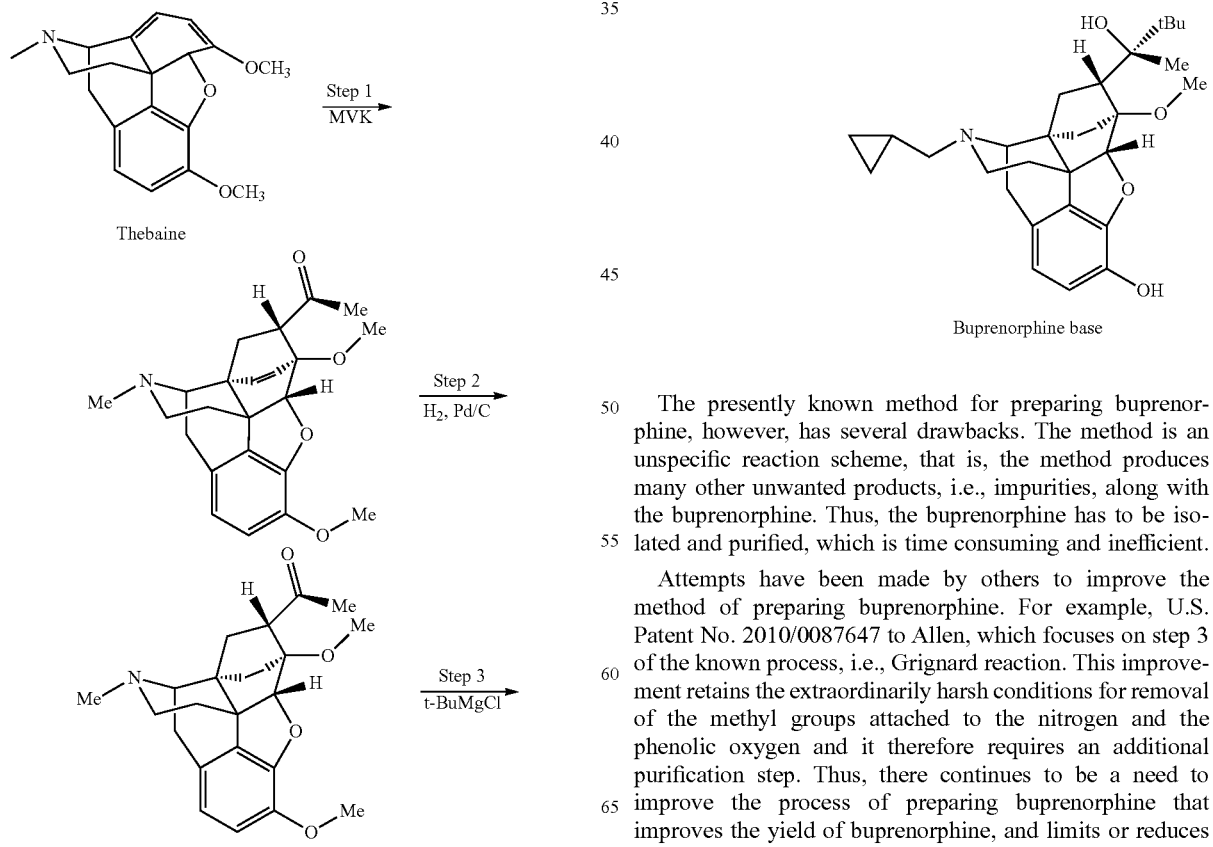

The presently known method for preparing buprenorphine, however, has several drawbacks. The method is an unspecific reaction scheme, that is, the method produces many other unwanted products, i.e., impurities, along with the buprenorphine. Thus, the buprenorphine has to be isolated and purified, which is time consuming and inefficient.

Attempts have been made by others to improve the method of preparing buprenorphine. For example, U.S. Patent No. 2010/0087647 to Allen, which focuses on step 3 of the known process, i.e., Grignard reaction. This improvement retains the extraordinarily harsh conditions for removal of the methyl groups attached to the nitrogen and the phenolic oxygen and it therefore requires an additional purification step. Thus, there continues to be a need to improve the process of preparing buprenorphine that improves the yield of buprenorphine, and limits or reduces the number of impurities formed during the process.

Definitions

Throughout this specification, the following abbreviations are used: cyanamide-norbuprenorphine-3-methyl ether (CMB); Norbuprenorphine 3-Methyl Ether (NME); Norbuprenorphine crude (NOC); Norbuprenorphine pure (NOP).

The point of attachment of a moiety or substituent is represented by "—". For example, —OH is attached through the oxygen atom.

"Alkyl" refers to a straight-chain, branched or cyclic saturated hydrocarbon group. In certain embodiments, the alkyl group may have from 1-20 carbon atoms, in certain embodiments from 1-15 carbon atoms, in certain embodiments, 1-8 carbon atoms. The alkyl group may be unsubstituted or substituted. Unless otherwise specified, the alkyl group may be attached at any suitable carbon atom and, if substituted, may be substituted at any suitable atom. Typical alkyl groups include but are not limited to methyl, ethyl, n-propyl, iso-propyl, cyclopropyl, n-butyl, iso-butyl, sec-butyl, tert-butyl, cyclobutyl, n-pentyl, cyclopentyl, n-hexyl, cyclohexyl and the like.

"Aryl" refers to an aromatic carbocyclic group. The aryl group may have a single ring or multiple condensed rings. In certain embodiments, the aryl group can have from 6-20 carbon atoms, in certain embodiments from 6-15 carbon atoms, in certain embodiments, 6-12 carbon atoms. The aryl group may be unsubstituted or substituted. Unless otherwise specified, the aryl group may be attached at any suitable carbon atom and, if substituted, may be substituted at any suitable atom. Examples of aryl groups include, but are not limited to, phenyl, naphthyl, anthracenyl and the like.

"Arylalkyl" refers to an optionally substituted group of the formula aryl-alkyl-, where aryl and alkyl are as defined above.

"Halo" or "halogen" refers to —F, —Cl, —Br and —I.

"Morphinan" refers to a compound comprising the core structure:

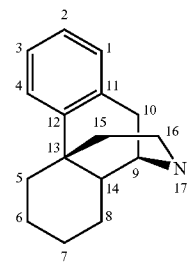

"Substituted" refers to a group in which one or more (e.g. 1, 2, 3, 4 or 5) hydrogen atoms are each independently replaced with substituents which may be the same or different. The substituent may be any group which tolerates the demethylation reaction conditions. Examples of substituents include but are not limited to —$R^a$, —O—$R^a$, —S—$R^a$, —$NR^aR^b$ and —$NHR^a$; wherein $R^a$ and $R^b$ are independently selected from the groups consisting of alkyl, aryl and arylalkyl, and wherein $R^a$ and $R^b$ may be unsubstituted or further substituted as defined herein.

SUMMARY OF THE INVENTION

In accordance with one aspect of the present invention, an improved method for the preparation of buprenorphine is provided that improves the overall yield of buprenorphine, and reduces the formation of impurities. Reduction of the formation of impurities is significant, as the process heretofore known in the art is prone to produce a great amount of impurities which requires purification and isolation processes.

Production of the impurities is believed to result in part from decomposition. It has been found by the present inventors that significant formation of impurities, and large yield losses occur during step 5 of the prior art buprenorphine reaction scheme. Without being held to any theory, it is believed that the drastic conditions at stage 5, i.e., demethylating the intermediate at 215° C., leads to both the decomposition and discoloration of the intermediates of the process, thereby increasing impurity formation. In one embodiment of the present invention, the improved method of preparing buprenorphine includes two separate reaction steps after stage 4 of the process. It has been found that this modification to the prior art process for making buprenorphine can occur at relatively mild conditions, and improves both overall yield of the product and reduces impurities formation. In some embodiments, a purification step is optional and not necessary.

In one embodiment, the improved method for preparing buprenorphine includes the following reaction steps shown below:

FIG. 2

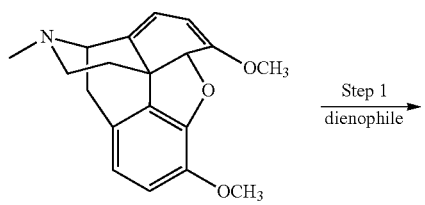

Thebaine

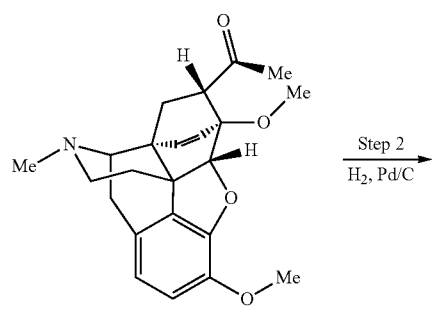

Formula II

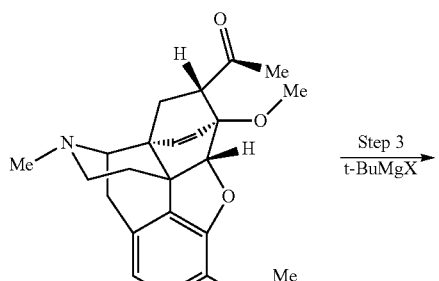

Formula III

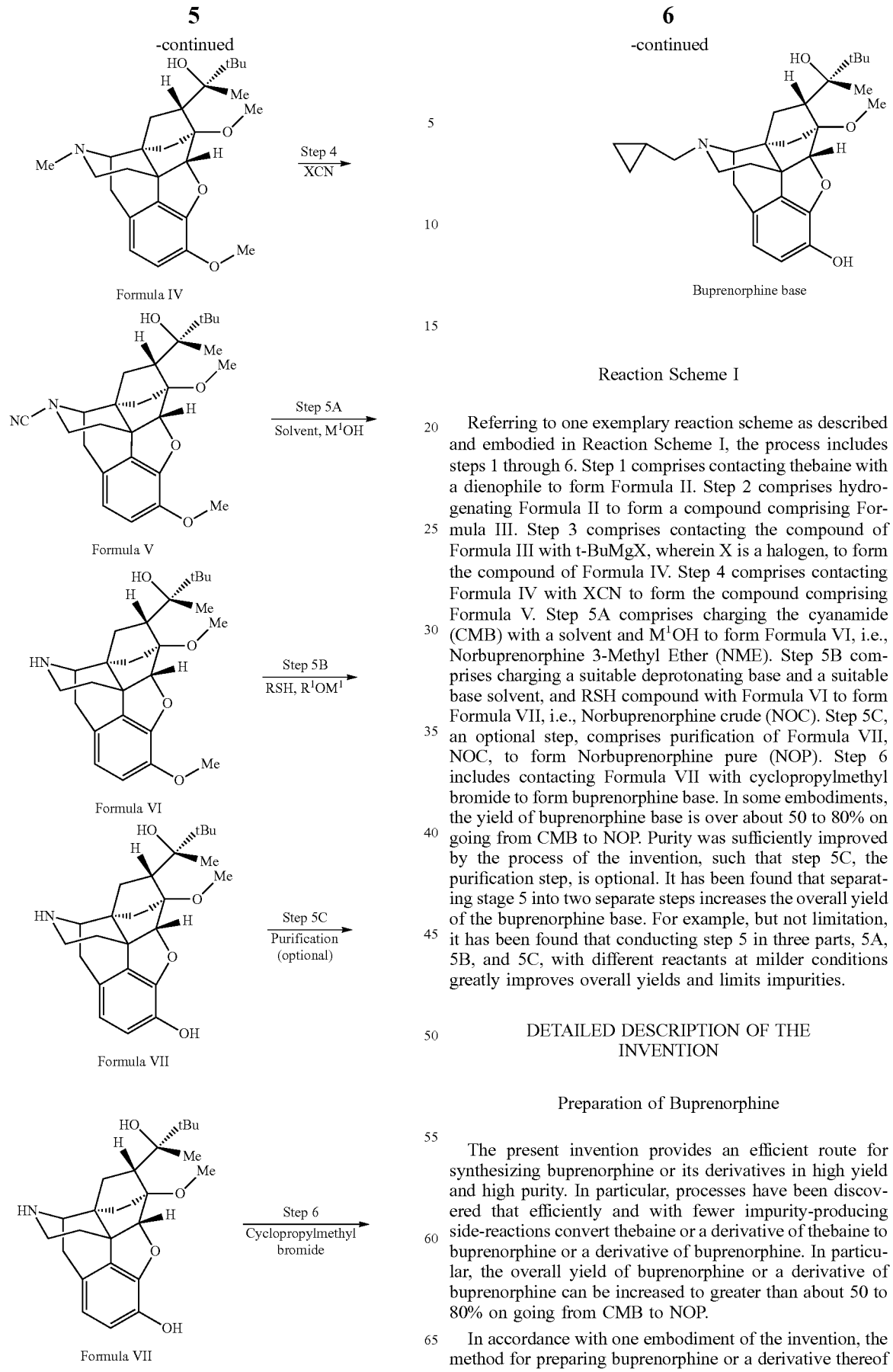

Reaction Scheme I

Referring to one exemplary reaction scheme as described and embodied in Reaction Scheme I, the process includes steps 1 through 6. Step 1 comprises contacting thebaine with a dienophile to form Formula II. Step 2 comprises hydrogenating Formula II to form a compound comprising Formula III. Step 3 comprises contacting the compound of Formula III with t-BuMgX, wherein X is a halogen, to form the compound of Formula IV. Step 4 comprises contacting Formula IV with XCN to form the compound comprising Formula V. Step 5A comprises charging the cyanamide (CMB) with a solvent and $M^1OH$ to form Formula VI, i.e., Norbuprenorphine 3-Methyl Ether (NME). Step 5B comprises charging a suitable deprotonating base and a suitable base solvent, and RSH compound with Formula VI to form Formula VII, i.e., Norbuprenorphine crude (NOC). Step 5C, an optional step, comprises purification of Formula VII, NOC, to form Norbuprenorphine pure (NOP). Step 6 includes contacting Formula VII with cyclopropylmethyl bromide to form buprenorphine base. In some embodiments, the yield of buprenorphine base is over about 50 to 80% on going from CMB to NOP. Purity was sufficiently improved by the process of the invention, such that step 5C, the purification step, is optional. It has been found that separating stage 5 into two separate steps increases the overall yield of the buprenorphine base. For example, but not limitation, it has been found that conducting step 5 in three parts, 5A, 5B, and 5C, with different reactants at milder conditions greatly improves overall yields and limits impurities.

DETAILED DESCRIPTION OF THE INVENTION

Preparation of Buprenorphine

The present invention provides an efficient route for synthesizing buprenorphine or its derivatives in high yield and high purity. In particular, processes have been discovered that efficiently and with fewer impurity-producing side-reactions convert thebaine or a derivative of thebaine to buprenorphine or a derivative of buprenorphine. In particular, the overall yield of buprenorphine or a derivative of buprenorphine can be increased to greater than about 50 to 80% on going from CMB to NOP.

In accordance with one embodiment of the invention, the method for preparing buprenorphine or a derivative thereof includes the following Reaction Scheme I.

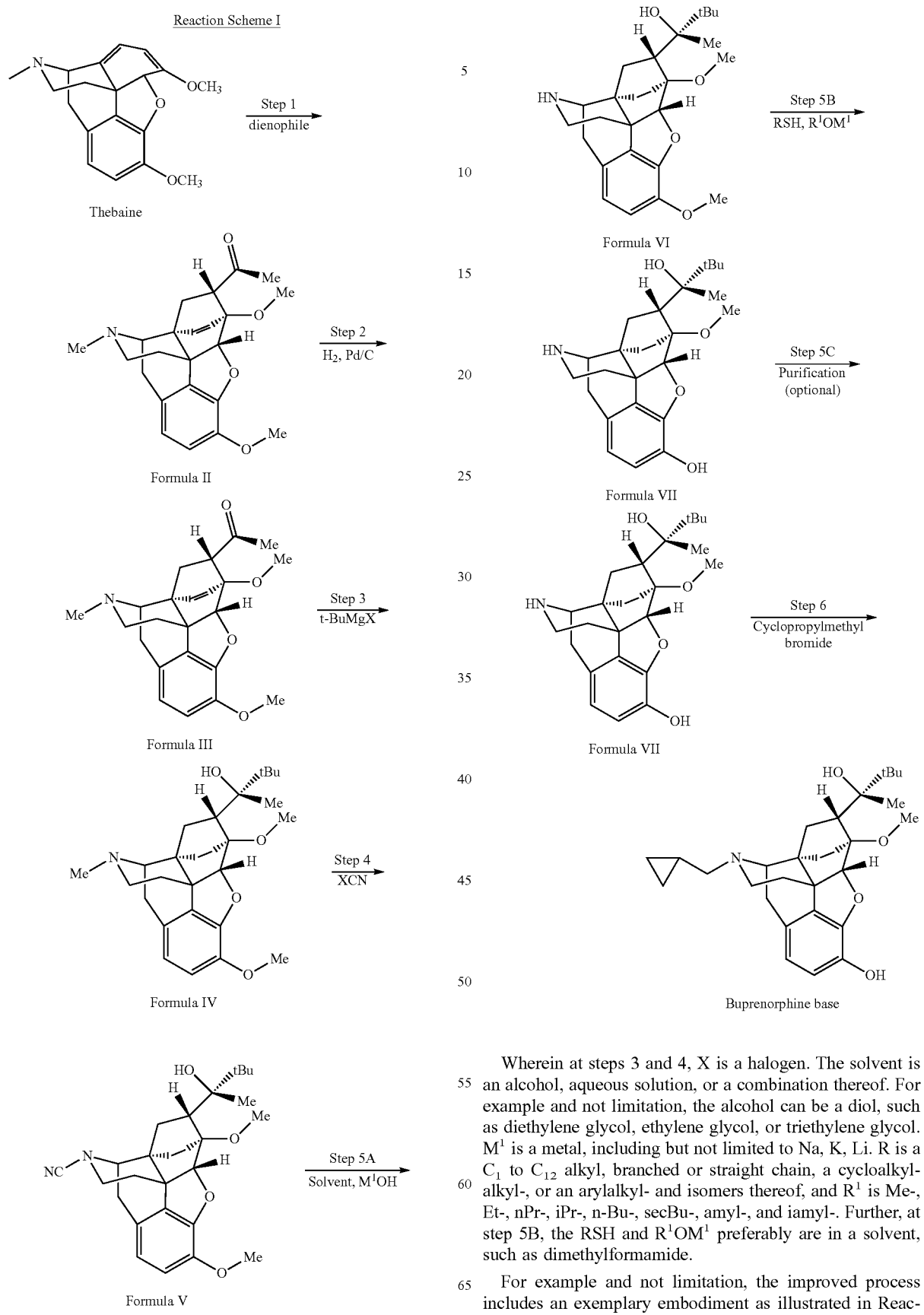

Wherein at steps 3 and 4, X is a halogen. The solvent is an alcohol, aqueous solution, or a combination thereof. For example and not limitation, the alcohol can be a diol, such as diethylene glycol, ethylene glycol, or triethylene glycol. $M^1$ is a metal, including but not limited to Na, K, Li. R is a $C_1$ to $C_{12}$ alkyl, branched or straight chain, a cycloalkyl-alkyl-, or an arylalkyl- and isomers thereof, and $R^1$ is Me-, Et-, nPr-, iPr-, n-Bu-, secBu-, amyl-, and iamyl-. Further, at step 5B, the RSH and $R^1OM^1$ preferably are in a solvent, such as dimethylformamide.

For example and not limitation, the improved process includes an exemplary embodiment as illustrated in Reaction Scheme II below.

9

Reaction Scheme II

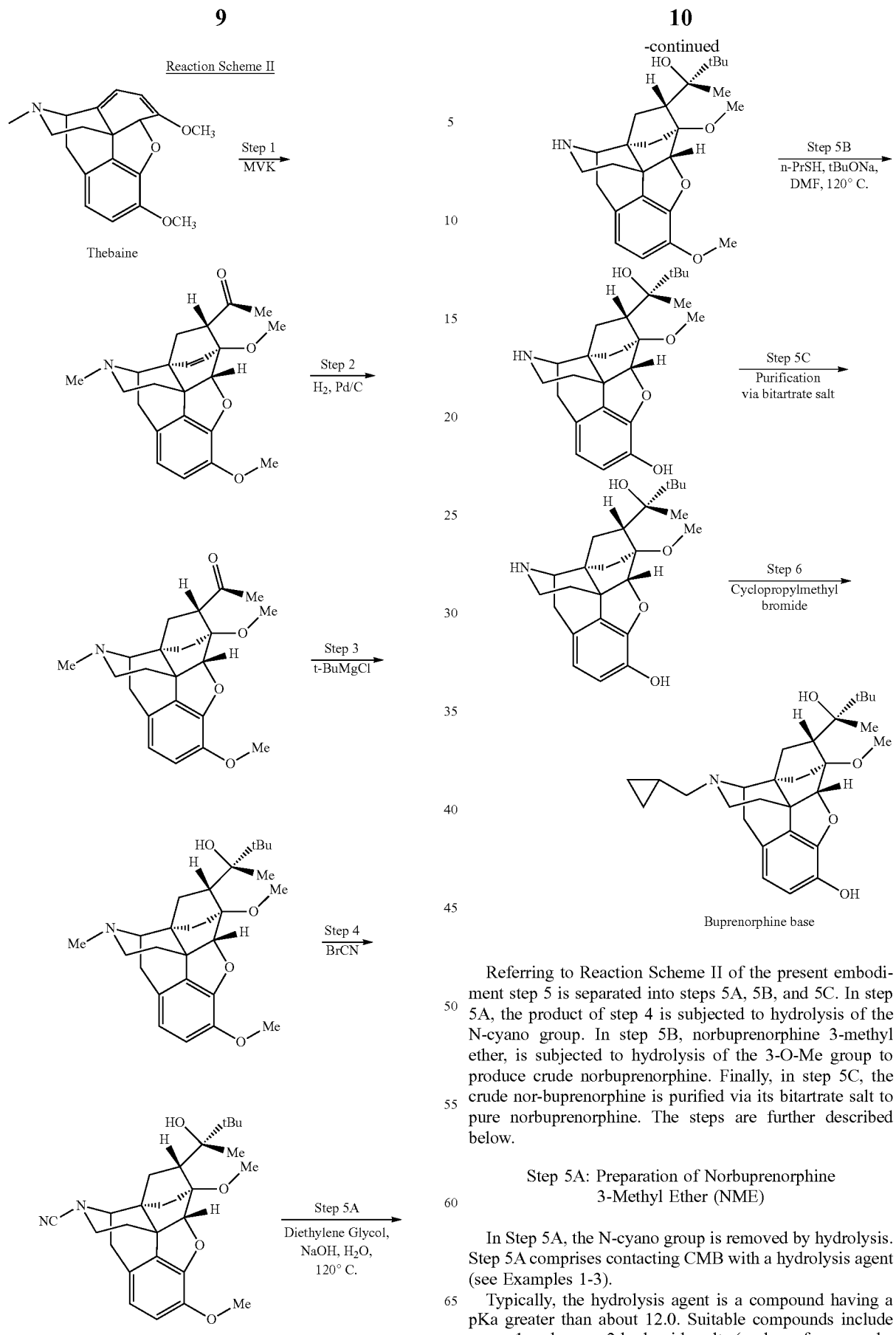

Referring to Reaction Scheme II of the present embodiment step 5 is separated into steps 5A, 5B, and 5C. In step 5A, the product of step 4 is subjected to hydrolysis of the N-cyano group. In step 5B, norbuprenorphine 3-methyl ether, is subjected to hydrolysis of the 3-O-Me group to produce crude norbuprenorphine. Finally, in step 5C, the crude nor-buprenorphine is purified via its bitartrate salt to pure norbuprenorphine. The steps are further described below.

Step 5A: Preparation of Norbuprenorphine 3-Methyl Ether (NME)

In Step 5A, the N-cyano group is removed by hydrolysis. Step 5A comprises contacting CMB with a hydrolysis agent (see Examples 1-3).

Typically, the hydrolysis agent is a compound having a pKa greater than about 12.0. Suitable compounds include group 1 and group 2 hydroxide salts (such as, for example, KOH and Ca(OH)$_2$); and metal oxides (such as, for example, lithium oxide, magnesium oxide, calcium oxide, and the like). In a preferred embodiment the hydrolysis agent may be a hydroxide of a group 1 or group 2 metal. In an exemplary embodiment, the hydrolysis agent may be sodium hydroxide. The molar ratio between CMB and the hydrolysis agent can and will vary. Typically, the molar ratio may vary from about 4 to about 8. In some exemplary embodiments, the ratio was 1:6.

The hydrolysis agent may be added to the reaction mixture as a solution of the hydrolysis agent in water. The concentration of the hydrolysis agent may range from about 10% to about 100%. In an exemplary embodiment, the hydrolysis agent may be a 50% solution of sodium hydroxide in water.

The CMB may be added to the reaction mixture either in solid form or as a solution in an appropriate organic solvent. In one exemplary embodiment, CMB was added to the reaction mixture as a solution of CMB in dichloromethane. The solution was extracted from the reaction mixture of the previous step in the overall scheme for preparation of buprenorphine.

The hydrolysis reaction mixture also includes an organic solvent. A variety of organic solvents are suitable for use in the process of the invention. Suitable organic solvents include, but are not limited to, ethylene glycol, diethylene glycol, triethylene glycol, 2-methoxyethanol, 1-methoxy-2-propanol, and combinations thereof. Lower boiling solvents such as methanol, ethanol, n-propanol, i-propanol are also suitable. However, reaction times may be longer and excessive. In an exemplary embodiment, the solvent may be diethylene glycol. The weight ratio of the solvent to the CMB may vary. In general, the weight ratio of the solvent to the CMB may range from about 2:1 to about 20:1.

In general, the hydrolysis reaction is conducted at a temperature that ranges from about 65° C. to about 125° C. In an exemplary embodiment, the reaction is conducted at about 116° C.

The reaction is preferably performed at ambient pressure, and preferably in an inert atmosphere (such as, for example, nitrogen, helium, or argon).

In general, the pH of the reaction mixture will be at least about pH 14. In an exemplary embodiment, there is an excess of strong base from beginning to the end, and the pH is always greater than 14. Depending on the hydrolysis agent, the pH of the mixture may be adjusted with an appropriate pH-modifying agent to attain the desired pH value. Those of skill in the art are familiar with suitable pH-modifying reagents.

Typically, the reaction is allowed to proceed for a sufficient period of time until the reaction is complete. More specifically, the reaction generally is allowed to proceed until the level of NME no longer increases. Those of skill in the art are familiar with suitable techniques to measure the amount of NME in the reaction mixture. One suitable technique is liquid chromatography. Typically, the reaction is allowed to proceed for a period of time that ranges from about one hour to about 48 hours. In an exemplary embodiment, the reaction is allowed to proceed for 20 hours.

Upon completion of the reaction, water is added to the reaction mixture and the reaction mixture is cooled. In an exemplary embodiment, the water is added dropwise. The temperature of the reaction mixture is allowed to fall until within the range about 95° C. to about 105° C. In an exemplary embodiment, the temperature is allowed to fall until within the range about 95° C. to about 100° C. The amount of water added to the mixture may vary. Typically, the weight ratio of water to the CMB ranges from about 5:1 to about 50:1. In an exemplary embodiment, the weight ratio of water to the CMB is 7.7:1.

After addition of the water, the reaction mixture is cooled over a period of time to cause precipitation of NME from the reaction mixture. The temperature of the reaction mixture is uniformly reduced until the temperature is within the range about 0° C. to about 10° C. In an exemplary embodiment, the temperature is uniformly reduced until the temperature is within the range 0° C. to 5° C. The period of time over which the reaction mixture is cooled may vary. Typically, the reaction mixture is cooled over a period of about 30 minutes to about three hours. In an exemplary embodiment, the reaction mixture is cooled over a period of two hours.

The precipitated NME may be easily separated from the reaction mixture using procedures well known to those of skill in the art.

Step 5B: Preparation of Crude Norbuprenorphine

In Step 5B, the 3-O-methyl group is removed to produce crude norbuprenorphine ("NOC"). Step 5B comprises contacting NME with an O-demethylation agent (see Examples 4-6). The O-demethylation agent can be, for example, a combination of a mercaptan and a strong organic base. Suitable mercaptans include mercaptans of alkanes, carboxylic acids. In an exemplary embodiment the O-demethylation agent may be n-propylmercaptan. The molar ratio between NME and the O-demethylation agent can and will vary. Typically, the molar ratio may vary from about 1:5 to about 1:1. In some exemplary embodiments, the ratio was about 1:2.

Suitable organic bases include lithium, sodium, and potassium salts of alcohols. In an exemplary embodiment the organic base was Sodium tert-butoxide.

The O-demethylation reaction includes an organic solvent. A variety of organic solvents are suitable for use in the process of the invention. Suitable organic solvents include, but are not limited to, dimethylformamide, dimethylacetamide, N-methylpyrrolidinone, DMSO, sulfolane, other dialkylamide solvents, and combinations, thereof. In an exemplary embodiment, the solvent was dimethylformamide. The weight ratio of the solvent to the NME may vary. In general, the weight ratio of the solvent to the NME may range from about 2:1 to about 20:1. In an exemplary embodiment, the weight ratio of the solvent to the NME was about 13:1.

The NME, the mercaptan, and the organic base may be added to the reaction mixture. In one particular embodiment, the NME is added last. In an exemplary embodiment, sodium tert-butoxide was added first, followed by the 1-propanethiol, followed by NME.

The reaction is preferably performed at ambient pressure, and preferably in an inert atmosphere (such as, for example, nitrogen, helium, or argon). In an exemplary embodiment, the reaction vessel was evacuated to 60 torr and filled with nitrogen three times before charging reactants.

In general, the O-demethylation reaction is conducted at a temperature that ranges from about 100° C. to about 125° C. In an exemplary embodiment, the reaction is conducted at a temperature between 115 and 125° C.

In general, the pH of the reaction mixture will be at least about pH 14. In this regard, the molar amount of base exceeds the molar amount of mercaptan.

Typically, the reaction is allowed to proceed for a sufficient period of time until the reaction is complete. More specifically, the reaction generally is allowed to proceed until the level of NOC no longer increases. Those of skill in the art are familiar with suitable techniques to measure the amount of NOC in the reaction mixture. One suitable technique is liquid chromatography. Typically, the reaction is allowed to proceed for a period of time that ranges from about one hour to about 48 hours. In an exemplary embodiment, the reaction is allowed to proceed for 12 hours.

Upon completion of the reaction, the reaction mixture is cooled. The temperature of the reaction mixture is allowed to fall until within the range about 60-100° C. In an exemplary embodiment, the temperature is allowed to fall until about 80° C.

After this cooling step, the reaction mixture is quenched by reducing the pH of the reaction mixture. For example but not limitation, sodium bicarbonate can be added to reduce the pH to approximately 7 or 9, so that strong base will not be an impurity in the precipitated product. The pH lowering agent may be dissolved in water. Examples of suitable pH lowering agents include sodium bicarbonate, mineral acid, e.g., dilute hydrochloric or sulfuric, or organic acid, e.g., acetic acid, preferably, the pH reducing agent is sodium bicarbonate. In an exemplary embodiment, the pH lowering agent was sodium bicarbonate dissolved in water.

The pH precipitation occurs over a period of time. The period of time over which the pH precipitation occurs may vary. Typically, the pH precipitation occurs over a period of 15 minutes to two hours. In an exemplary embodiment, the pH precipitation occurred over a course of one hour.

After the pH precipitation, the reaction mixture is cooled over a period of time to further encourage precipitation of NOC from the reaction mixture. The temperature of the reaction mixture is uniformly reduced until the temperature is within the range about 0° C. to about 10° C. In an exemplary embodiment, the temperature is uniformly reduced until the temperature is within the range 0° C. to 5° C. The period of time over which the reaction mixture is cooled may vary. Typically, the reaction mixture is cooled over a period of about 30 minutes to about three hours. In an exemplary embodiment, the reaction mixture is cooled over a period of two hours.

The precipitated NOC may be easily separated from the reaction mixture using procedures well known to those of skill in the art.

The NOC thus produced may be used without purification in the sixth and final step of the buprenorphine process described above, or it may be further purified before such use.

Step 5C: Purification of Crude Norbuprenorphine to Pure Norbuprenorphine

In step 5C, the crude norbuprenorphine is purified to produce pure norbuprenorphine (NOP). The crude norbuprenorphine is purified by converting it to an organic acid salt, followed by production of the purified free-base norbuprenorphine.

The organic acid salt is produced by contacting the NOC with an organic acid. Typically, the organic acid used to form the salt is a carboxylic acid or a di-carboxylic acid. Suitable acids include tartaric acid. In an exemplary embodiment the organic acid was L-tartaric acid. In an exemplary embodiment, the ratio was about 1:1.

The salt formation reaction includes an organic solvent. A variety of organic solvents are suitable for use in the process of the invention. Suitable organic solvents include, but are not limited to, polar solvents, small alcohols and acetone, and combinations, thereof. In an exemplary embodiment, the solvent was isopropyl alcohol. The weight ratio of the solvent to the NOC may vary. In general, the weight ratio of the solvent to the NME may range from about 5:1 to about 30:1. In an exemplary embodiment, the weight ratio of the solvent to the NME was about 20:1.

In general, the salt formation reaction is conducted at a temperature that ranges from about 60° C. to 80° C. In an exemplary embodiment, the reaction was conducted at a temperature between 70° C. and 75° C.

Typically, the reaction is allowed to proceed for a sufficient period of time until the reaction is complete. More specifically, the reaction generally is allowed to proceed until cloudiness is seen and crystal formation has begun. If cloudiness is not observed, those of skill in the art are familiar with techniques for seeding crystallization of the reaction system. In an exemplary embodiment, a small amount of the solution was withdrawn and scratched to created seed crystals, then returned to the flask.

Upon completion of the reaction, the reaction mixture is cooled over a period of time to further encourage precipitation of the salt from the reaction mixture. The temperature of the reaction mixture is allowed to fall until within the range about 40-55° C. In an exemplary embodiment, the temperature is allowed to fall until between 50° C. and 80° C. The period of time over which the reaction mixture is cooled may vary. Typically, the reaction mixture is cooled over a period of about 30 minutes to about three hours. In an exemplary embodiment, the reaction mixture is cooled over a period of two hours.

The precipitated salt may be easily separated from the reaction mixture using procedures well known to those of skill in the art.

The salt is converted to NOP by contacting the salt with an inorganic base. Typically, the inorganic base is a hydroxide of a group 1 or group 2 metal. In an exemplary embodiment, the inorganic base may be sodium hydroxide.

The base regeneration from the salt reaction uses water as a solvent. The weight ratio of the solvent to the salt may vary. In general, the weight ratio of the solvent to the salt may range from about 20:1 to about 100:1. In an exemplary embodiment, the weight ratio of the solvent to the salt was about 47:1.

In general, the base regeneration from the salt reaction is conducted at a temperature that ranges from about 40° C. to about 80° C. The temperature may vary within this range during the course of the reaction. In an exemplary embodiment, the reaction was conducted at a temperature between 45° C. and 55° C. in an initial portion of the reaction, and between 65° C. and 75° C. in a later portion of the reaction.

To produce the desired NOP, the inorganic base is added to a solution of the salt to adjust the pH to a value above 9.0. In an exemplary embodiment, the pH was maintained within the range 9.0 to 9.5. This pH adjustment causes precipitation.

The reaction is allowed to proceed at the designated pH for a sufficient period of time until material forms a more readily filterable precipitate. More specifically, the reaction generally is allowed to proceed until the solution becomes thick with precipitate, then thins out. In an exemplary embodiment, this process took twenty minutes.

Upon completion of the reaction, the reaction mixture is filtered without cooling. The resulting filtrate may be washed with water and dried using procedures well known to those of skill in the art.

In one embodiment, an improved process for preparing buprenorphine is provided, wherein the steps include contacting thebaine with a dienophile to form Formula II, hydrogenating Formula II to form a compound comprising Formula III, contacting the compound of Formula IV with XCN to form the compound of Formula V, the improvement comprising subjecting the compound of Formula V to hydrolysis, e.g., of the N-cyano group, and further subjecting the product of the first hydrolysis to a second hydrolysis, e.g., the 3-O-Me group. In this regard, the product of the two hydrolysis steps produces norbuprenorphine. The norburprenorphine is contacted with an agent to form buprenorphine base. In some embodiments, the nor-burprenorphine is purified.

3-O-demethylation of Morphinans

In another aspect, the present invention provides a process for the preparation of a compound of formula (Ib),

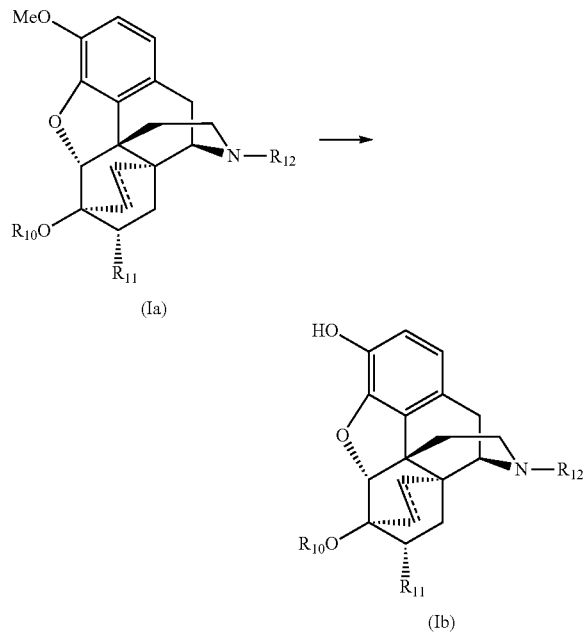

wherein:
$R_{10}$ is a straight-chain, branched or cyclic $C_1$-$C_{20}$ alkyl;
$R_{11}$ is —C($R_{13}$)($R_{14}$)(OH) or a protected —C(=O)($R_{15}$);
$R_{12}$ is H or CN;
$R_{13}$ is a straight-chain, branched or cyclic $C_1$-$C_{20}$-alkyl;
$R_{14}$ is a straight-chain, branched or cyclic $C_1$-$C_{20}$-alkyl;
$R_{15}$ is a straight-chain, branched or cyclic $C_1$-$C_{20}$-alkyl and
=== is a double bond or a single bond;
the process comprising:
 i. reacting a compound of formula (Ia) with a thiolate in a suitable polar aprotic solvent, wherein the thiolate is selected from the group consisting of an optionally substituted $C_1$-$C_{20}$-alkylthiolate, an optionally substituted $C_6$-$C_{20}$-arylthiolate or an optionally substituted $C_7$-$C_{30}$-arylalkylthiolate; and
 ii. treating the reaction mixture of step (i) with a protonating agent to give the compound of formula (Ib).

$R_{10}$ is a straight-chain, branched or cyclic $C_1$-$C_{20}$ alkyl, preferably a straight-chain $C_1$-$C_{20}$ alkyl. In one embodiment, $R_{10}$ is a $C_1$-$C_{15}$ alkyl group, such as a $C_1$-$C_{10}$ alkyl, for example, a $C_1$-$C_5$ alkyl. In one preferred embodiment, $R_{10}$ is -Me.

$R_{11}$ is —C($R_{13}$)($R_{14}$)(OH), wherein $R_{13}$ and $R_{14}$ are independently straight-chain, branched or cyclic $C_1$-$C_{20}$-alkyl groups. In one embodiment, $R_{11}$ is

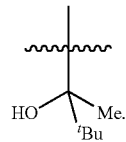

In another embodiment, $R_{11}$ is

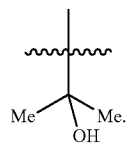

In yet another embodiment, $R_{11}$ is

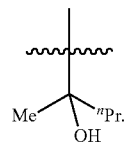

$R_{11}$ can be a protected —C(=O)($R_{15}$). In one embodiment, the keto group may be protected as an acetal or a ketal as described below. In one preferred embodiment, $R_{15}$ is -Me. In one embodiment, the protecting group may be removed by methods known in the art to form —C(=O)($R_{15}$).

Interestingly, the present inventors have found that when the amino group of compound (Ia) is substituted with an -alkylcycloalkyl group such as -methyl-cyclopropane, the 3-O-demethylation reaction does not appear to work efficiently.

The O-demethylation step may affect other substituents of the morphinan susceptible to basic conditions or reactive towards nucleophiles, such as keto groups. Thus, it is may be desirable to first protect the keto group with a suitable protecting group which may be optionally removed after the O-demethylation step is completed. Protecting groups are known in the art and methods for their introduction and removal are described in standard references such as "Greene's Protective Groups in Organic Synthesis", P. G. M. Wuts and T. W. Greene, 4th Edition, Wiley. Suitable keto protecting groups include but are not limited to acetals and ketals. For example, substituted or unsubstituted, straight-chain or branched $C_1$-$C_{20}$-alkanols, substituted or unsubstituted, straight-chain or branched 1,2-($C_1$-$C_{20}$)-alkyl-diols (for example, ethylene glycol or 1,2-propanediol), or substituted or unsubstituted, straight-chain or branched 1,3-($C_1$-$C_{20}$)-alkyldiols may be conveniently utilized to form suitable acetals or ketals. A diol reacts to form a ring and in this instance, the ketal comprises substituted or unsubstituted chiral or achiral bridges which are derived, for example, from the skeletons —(CH$_2$)$_n$— (n=2, 3 or 4), —CH(CH$_3$)CH(CH$_3$)—, —CH(CH$_3$)CH$_2$CH(CH$_3$)—, —CMe$_2$-, —CHMe-, no limitation being implied by this listing.

The process of the present invention can be performed on morphinans comprising unprotected hydroxyl groups. However, if desired, the hydroxy groups may be first protected with a protecting group which may be optionally removed after the O-demethylation step is completed. Suitable protecting groups include but are not limited to alkyl, aryl (e.g. phenyl), benzyl, acyl and silyl groups. Other suitable protecting groups are described in Wuts and Greene above.

The thiolate does not appear to react with unconjugated —C=C— double bonds. Accordingly, the process of the present invention may be carried out on morphinans comprising this functional group. In one embodiment, therefore, === is a —C=C— double bond. Alternatively, === can be a —C—C— single bond.

The thiolate is selected from the group consisting of an optionally substituted $C_1$-$C_{20}$-alkylthiolate, an optionally substituted $C_6$-$C_{20}$-arylthiolate or an optionally substituted $C_7$-$C_{30}$-arylalkylthiolate. In one preferred embodiment, the thiolate is unsubstituted.

In one embodiment, the thiolate is substituted. An example of a substituted alkylthiolate is $MeO_2C$—$CH_2CH_2S^-$.

In one embodiment, the alkyl group of the alkylthiolate comprises 2 to 4 carbon atoms, for example, propanethiolate. In another embodiment, the alkyl group of the alkylthiolate comprises greater than 4 carbon atoms, such as 5 or more carbons, for example, 8 or more carbons. In one preferred embodiment, the alkylthiolate is a $C_{10}$-$C_{20}$-alkylthiolate. In one particularly preferred embodiment, the alkylthiolate is a dodecanethiolate salt. Unlike other thiolates, the use of dodecanethiolate is advantageous as it is significantly less odorous than other thiolates.

An example of a suitable $C_6$-$C_{20}$-arylthiolate includes but is not limited to phenylthiolate. An example of a suitable $C_7$-$C_{30}$-arylalkylthiolate includes but is not limited to phenylmethylthiolate.

In some embodiments, the thiolate may be an alkylthiolate, arylthiolate or arylalkylthiolate tethered to an insoluble support. In one embodiment, the insoluble support is a suitable organic support (such as polystyrene). In another embodiment, the insoluble support is a suitable inorganic support.

The counter cation of the thiolate is typically an alkali metal cation i.e. $Li^+$, $Na^+$ or $K^+$.

The thiolate may be a commercially available thiolate salt. Alternatively, the thiolate may be prepared from a thiol and a base which is capable of deprotonating the thiol. Suitable bases are generally those where the pKa of the conjugate acid is greater than about four units higher than the pKa of the thiol. In this regard, the approximate pKa of a typical alkylthiol is about 10. Consequently, deprotonation of the alkylthiol may be achieved with the use of a base where the pKa of the conjugate acid is greater than about 14. Examples of suitable bases include but are not limited to alkali metal alkoxides (e.g. sodium or potassium methoxide, sodium or potassium ethoxide, sodium or potassium propoxide or sodium or potassium butoxide), alkali metal hydroxides (such as sodium or potassium hydroxide), alkali metal hydrides (e.g. sodium hydride), organolithium reagents (such as butyllithium) or alkali metal amides (e.g. $NaNH_2$ or $KNH_2$).

The molar ratio between the compound (Ia) and the thiolate can and will vary. Typically, the molar ratio will vary from about 1:5 to about 1:1. In some exemplary embodiments, the ratio may be about 1:3, and in others, about 1:1.5.

The compound of formula (Ia) is reacted with the thiolate in a suitable polar aprotic solvent. By "polar aprotic solvent" we mean a liquid medium with a high dielectric constant and dipole moment which does not have an acidic hydrogen. The high polarity of the solvent allows it to dissolve charged species such as nucleophiles (i.e. the thiolate) but the absence of an acidic hydrogen increases the reactivity of nucleophiles as they are less solvated in solution. The polar aprotic solvent is also able to dissolve the compound of formula (Ia) to form solutions which are preferably in the range of about 0.01-2 mol/L, preferably about 0.05-1.0 mol/L, more preferably about 0.1-0.8 mol/L. While a small quantity of water may be present in the O-demethylation reaction mixture (i.e. <0.55% w/w water), the solvent is preferably anhydrous. Suitable polar aprotic solvents preferably have boiling points at atmospheric pressure (i.e. $1.0135 \times 10^5$ Pa) above 140° C. and more preferably above 150° C. Such solvents generally allow the reaction to be carried out at the optimum temperature to minimize reaction time and impurity generation. Preferred examples are dialkylamide solvents (e.g. dimethylformamide or dimethylacetamide), or cycloalkylamide solvents (e.g. N-methyl-2-pyrrolidone) or combinations thereof. Other examples include dimethylsulfoxide, sulfolane, hexamethylphosphoramide or combinations thereof.

The reaction of step (i) is preferably performed at ambient pressure, and preferably in an inert atmosphere (such as, for example, nitrogen, helium or argon).

In general, the reaction of step (i) may be conducted at a temperature in the range of about 100° C. to about 130° C. In an exemplary embodiment, the reaction is conducted at a temperature between about 115° C. and about 125° C.

Typically the reaction of step (i) is allowed to proceed for a sufficient period of time until the reaction is complete. More specifically, the reaction generally is allowed to proceed until the level of compound of formula (Ib) no longer increases. Those of skill in the art are familiar with suitable techniques to measure the amount of compound (Ib) in the reaction mixture. One suitable technique is HPLC. Typically, the reaction is allowed to proceed for a period of time that ranges from about one hour to about 48 hours. In an exemplary embodiment, the reaction is allowed to proceed for 12 hours or less. In certain embodiments, the reaction is allowed to proceed for 6 hours or less.

A variety of conditions may be selected in order to help minimize or eliminate the production of impurities by over demethylation at C-6. These conditions include the temperature at which step (i) is conducted and/or the time for which the reaction is allowed to proceed.

In step (ii) the reaction mixture of step (i) is treated with a protonating agent to give the compound of formula (Ib). Without wishing to be bound by theory, it is believed that the protonating agent quenches the 3-O-phenolate anion to provide the compound (Ib). Suitable protonating agents include aqueous solutions of an alkali metal bicarbonate (e.g. sodium or potassium bicarbonate). Without wishing to be bound by theory, it is believed that the bicarbonate decomposes to form a carbonate and protons.

The reactants may be added in any suitable order. In one preferred process of the invention, the compound (Ia) with a solvent (if used) is added to a reaction mixture of the thiolate in solvent and is reacted for a time and under conditions sufficient for compound (Ia) to be O-demethylated, followed by the addition of the protonating agent in order to form the compound (Ib).

Upon completion of the reaction, the reaction mixture may be treated as generally described above in connection with Step 5B, i.e. the preparation of crude norbuprenorphine.

Various compounds of formula (Ia) may be treated according to the processes described herein to yield compounds of formula (Ib) as illustrated below:
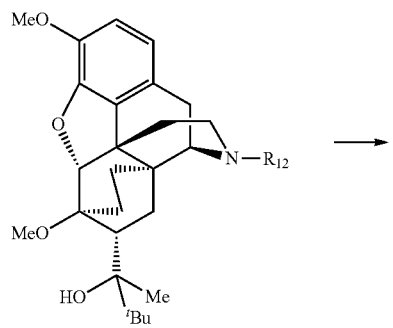
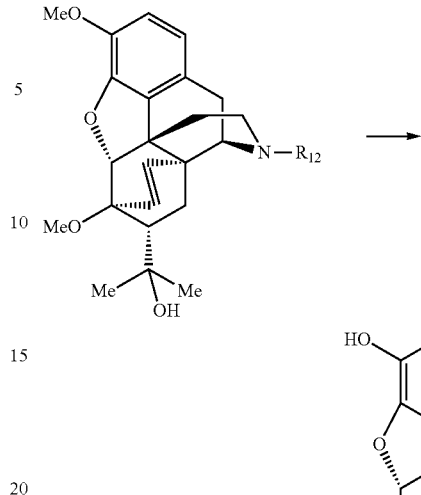
where R$_{12}$ = H or CN
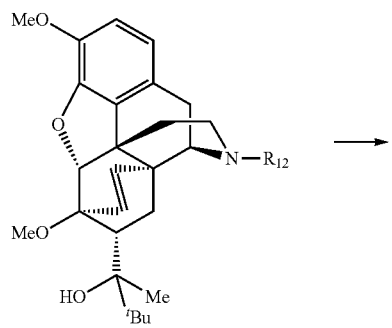
where R$_{12}$ = H or CN
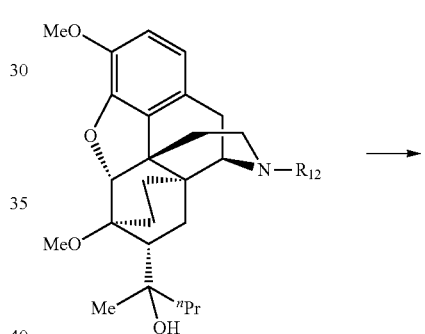
where R$_{12}$ = H or CN
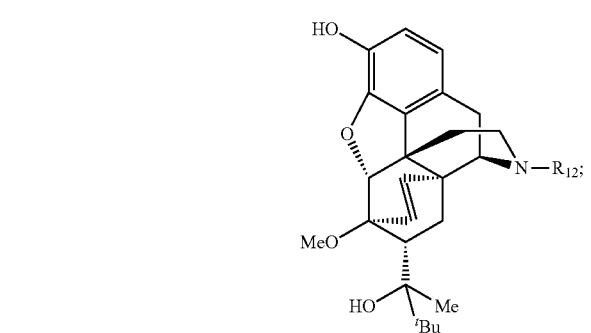
where R$_{12}$ = H or CN
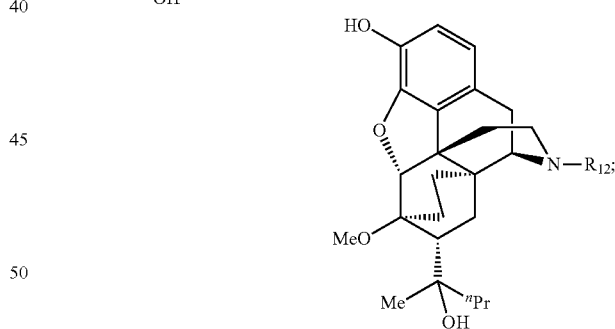

-continued

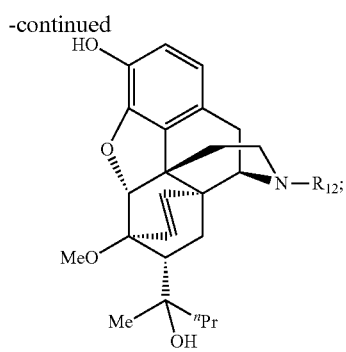

where $R_{12}$ = H or CN

In another aspect, the present invention provides a process for the preparation of a compound of formula (IIb),

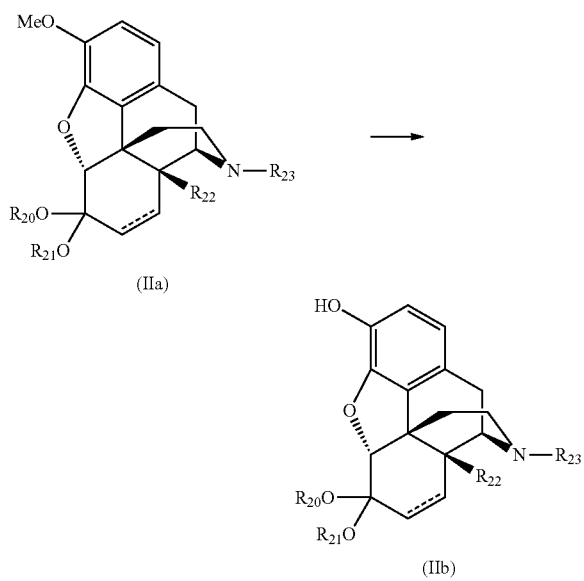

wherein:
$R_{20}$ and $R_{21}$ are independently selected from substituted or unsubstituted $C_1$-$C_{20}$ alkyl or $R_{20}$ and $R_{21}$ are interconnected to form a ring;
$R_{22}$ is H or OH;
$R_{23}$ is selected from the group consisting of H, CN, substituted $C_1$-$C_{20}$ alkyl, unsubstituted $C_1$-$C_{20}$ alkyl, substituted $C_4$-$C_{20}$-alkyl-cycloalkyl, unsubstituted $C_4$-$C_{20}$-alkyl-cycloalkyl and allyl;
--- is a double bond or a single bond;
the process comprising:
  i. reacting a compound of formula (IIa) with a thiolate in a suitable polar aprotic solvent, wherein the thiolate is selected from the group consisting of an optionally substituted $C_1$-$C_{20}$-alkylthiolate, an optionally substituted $C_6$-$C_{20}$-arylthiolate or an optionally substituted $C_7$-$C_{30}$-arylalkylthiolate; and
  ii. treating the reaction mixture of step (i) with a protonating agent to give the compound of formula (IIb).

When $R_{20}$ and $R_{21}$ are interconnected to form a ring, the two groups may form a ketal as generally described above. In one embodiment, the groups may form substituted or unsubstituted chiral or achiral bridges which are derived, for example, from the skeletons —$(CH_2)_n$— (n=2, 3 or 4), —CH($CH_3$)CH($CH_3$)—, —CH($CH_3$)$CH_2$CH($CH_3$)—, —$CMe_2$-, —CHMe-, no limitation being implied by this listing.

In one embodiment, $R_{22}$ is H. In another embodiment, $R_{22}$ is OH.

In one embodiment, $R_{23}$ may be H, in another embodiment CN, and in yet another embodiment allyl (i.e. —$CH_2$CH=$CH_2$). When $R_{23}$ is an unsubstituted $C_1$-$C_{20}$ alkyl, $R_{23}$ is preferably -Me. When $R_{23}$ is an unsubstituted $C_4$-$C_{20}$-alkyl-cycloalkyl, $R_{23}$ is preferably cyclopropylmethyl-

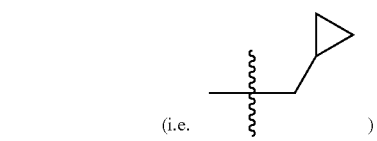 [SMILES: *CC1CC1]

or cyclobutylmethyl-

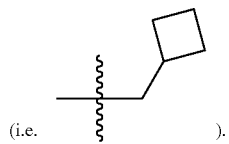

In one embodiment, --- is a —C=C— double bond. In another embodiment, --- is a —C—C— single bond.

The compound (IIb) may be deprotected to form a keto group at C-6. In one embodiment, therefore, the process further comprises converting the compound of formula (IIb) to a compound of formula (IIc):

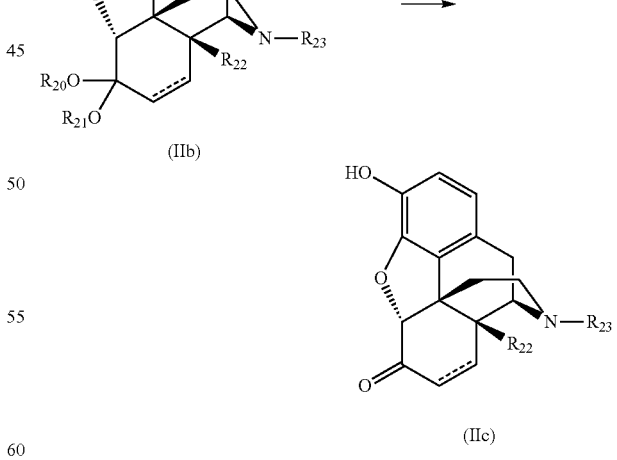

The compound (IIb) may be isolated and optionally purified before being deprotected. In this instance, the deprotection may be performed by methods known in the art. Alternatively, the 3-O-demethylation conditions of step (i) and/or (ii) may adapted such that the deprotection step also occurs in a one-pot reaction.

In another aspect, the present invention provides a process for the preparation of a compound of formula (IIIb),

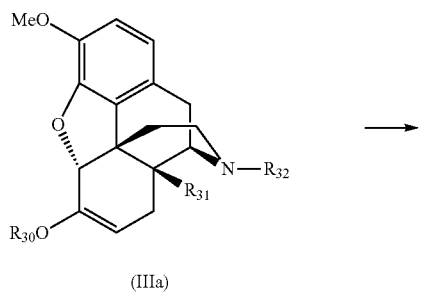

(IIIa)

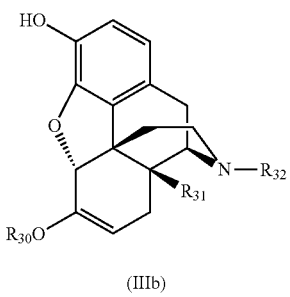

(IIIb)

wherein:
R$_{30}$ is an alcohol protecting group;
R$_{31}$ is H or OH; and
R$_{32}$ is selected from the group consisting of H, CN, substituted C$_1$-C$_{20}$ alkyl, unsubstituted C$_1$-C$_{20}$ alkyl, substituted C$_4$-C$_{20}$-alkyl-cycloalkyl, unsubstituted C$_4$-C$_{20}$-alkyl-cycloalkyl and allyl;
the process comprising:
  i. reacting a compound of formula (IIIa) with a thiolate in a suitable polar aprotic solvent, wherein the thiolate is selected from the group consisting of an optionally substituted C$_1$-C$_{20}$-alkylthiolate, an optionally substituted C$_6$-C$_{20}$-arylthiolate or an optionally substituted C$_7$-C$_{30}$-arylalkylthiolate; and
  ii. treating the reaction mixture of step (i) with a protonating agent to give the compound of formula (IIIb).

R$_{30}$ is an alcohol protecting group. In one embodiment, R$_{30}$ is selected from substituted or unsubstituted C$_1$-C$_{20}$ alkyl. Alternatively, R$_{30}$ may be a silyl protecting group such as a substituted or unsubstituted (C$_1$-C$_{20}$-alkyl)$_3$Si— (such as Me$_3$Si— (TMS), $^t$BuMe$_2$Si— (TBDMS) or $^i$Pr$_3$Si— (TIPS)), a substituted or unsubstituted (C$_1$-C$_{20}$-alkyl)(C$_6$-C$_{20}$-aryl)$_2$Si— (for example, $^t$BuPh$_2$Si— (TBDPS)) or a substituted or unsubstituted (C$_1$-C$_{20}$-alkyl)$_2$(C$_6$-C$_{20}$-aryl)Si—.

In one embodiment, R$_{31}$ is H. In another embodiment, R$_{31}$ is OH.

In one embodiment, R$_{32}$ may be H, in another embodiment CN, and in yet another embodiment allyl (i.e. —CH$_2$CH=CH$_2$). When R$_{32}$ is an unsubstituted C$_1$-C$_{20}$ alkyl, R$_{32}$ is preferably -Me. When R$_{32}$ is an unsubstituted C$_4$-C$_{20}$-alkyl-cycloalkyl, R$_{32}$ is preferably cyclopropylmethyl-

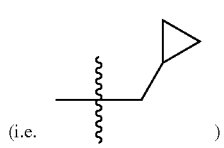 [SMILES: *CC1CC1]

(i.e.

or cyclobutylmethyl-

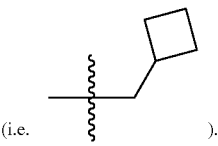

(i.e.          ).

The compound (IIIb) may be deprotected to form a keto group at C-6. In one embodiment, therefore, the process further comprises converting the compound of formula (IIIb) to a compound of formula (IIIc):

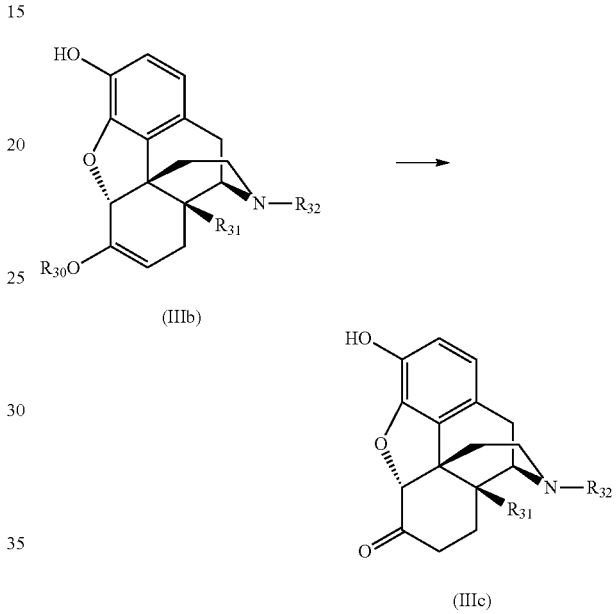

The compound (IIIb) may be isolated and optionally purified before being deprotected. In this instance, the deprotection may be performed by methods known in the art. Alternatively, the 3-O-demethylation conditions of step (i) and/or (ii) may adapted such that the deprotection step also occurs in a one-pot reaction.

The reaction conditions for steps (i) and (ii) in the preparation of compounds (IIb) or (IIIb) are as generally described above for the preparation of compound (Ib).

Impurities which may be specified in the Official Monographs for morphinans such as oxymorphone include α,β-unsaturated ketones (ABUKs), such as 14-hydroxymorphinone. There has been much recent concern over ABUKs due to their proposed biological activities as carcinogens. As such, there is a continuing need to develop processes which produce low ABUK morphinans, in particular low ABUK oxymorphone alkaloid or hydrochloride. Low ABUK oxymorphone may be prepared using the processes of the present invention starting from low ABUK oxycodone. For example, low ABUK oxycodone may be protected to form compounds (IIa) or (IIIa). Low ABUK oxymorphone therefore may be prepared via compounds (IIb) or (IIIb).

Thus, in one embodiment, the oxymorphone alkaloid prepared according to the present invention comprises ≤about 25 ppm of an α,β-unsaturated ketone, such as ≤about 20 ppm of an α,β-unsaturated ketone, for example, ≤about 15 ppm of an α,β-unsaturated ketone. In one preferred embodiment, the oxymorphone alkaloid comprises ≤about 10 ppm of an α,β-unsaturated ketone. In another embodiment, the oxymorphone alkaloid is substantially free of an α,β-unsaturated ketone.

EXAMPLES

The following examples are included to demonstrate exemplary embodiments of the invention. It should be appreciated by those of skill in the art that the techniques disclosed in the following examples represent techniques discovered by the inventors to function well in the practice of the invention. Those of skill in the art should, however, in light of the present disclosure, appreciate that many changes could be made in the specific embodiments that are disclosed and still obtain a like or similar result without departing from the spirit and scope of the invention, therefore all matter set forth is to be interpreted as illustrative and not in a limiting sense.

Example 1: CMB Decyanation 45.26 g CMB (100 mmol) was added to 400 mL ethylene glycol and 48 g of 50% NaOH/$H_2O$ (600 mmol), stirred under nitrogen, and slowly heated to 120° C. The reaction mixture was maintained at 115-125° C. for approximately 12 hours, after which it was allowed to cool to room temperature. The mixture was re-heated to 120° C. and 400 mL water was added dropwise over the course of approximately 40 minutes, during which time the temperature was reduced to 100-105° C. The mixture was cooled to 4° C. over approximately 1.5 hours. The resulting precipitate was filtered, washed with water, and dried in a 60° C. vacuum oven. The result was 40.99 g NME (95.9% yield), and its liquid chromatography-measured purity at 210 nm was 96.04%.

Example 2: CMB Decyanation 9.05 g CMB (20 mmol) was added to 100 mL ethylene glycol and 9.6 g of 50% NaOH/$H_2O$ (120 mmol), stirred under nitrogen, and maintained at 130° C. After approximately 55 minutes, some water was allowed to evaporate, and an odor of ammonia was detected in the escaping gas. After another approximately one hour and ten minutes, the reaction mixture was allowed to cool to room temperature. The resulting precipitate was washed with water and dried in a vacuum oven at 60° C. The resulting product was 7.99 g (93.5% yield), and its liquid chromatography-measured purity at 210 nm was 96.22%.

Example 3: CMB Decyanation 45.26 g CMB (100 mmol) was added to 350 mL 2-methoxyethanol and 48 g of 50% NaOH/$H_2O$ (600 mmol), stirred under nitrogen, and maintained at approximately 110-120° C. After approximately 20 hours, 100 mL of water was added, and the temperature to drop to 93.5° C. The mixture was kept at 95-100° C. and 250 mL more of water was added for a total of 350 mL water. The reaction mixture was cooled to 3° C. over 1.5 hours. The resulting precipitate was filtered, washed with water, and dried at 60° C. in a vacuum oven for 3 hours. The resulting product was 40.56 g (94.9% yield), and its liquid chromatography-measured purity at 210 nm was 97.77%.

Example 4: NME O-demethylation with nPrSNa 2.14 g NME (5 mmol), 0.98 g sodium n-propylmercaptide (10 mmol), and 35 mL DMF were stirred under nitrogen. The reaction mixture was heated to 120° C. and refluxed for 12 hours and allowed to cool to room temperature. 14 mL of 6% $NaHCO_3$ (10 mmol) was added, then 56 mL water. The mixture was cooled to 2° C. The resulting precipitate was filtered, washed well with water, and dried to produce 1.58 g NOC (76% yield), and its liquid chromatography-measured purity at 210 nm was 92.10%.

Example 5: NME O-demethylation with PrSH/NaOt-Bu 21.38 g NME (50 mmol) and 9.61 g NaOt-Bu (100 mmol) were dissolved in 350 mL DMF. 9.5 mL 1-propanethiol (105 mmol) were added, producing a purple solution. The reaction mixture was stirred under Nitrogen, heated to 120° C. over approximately one hour, refluxed at 115-125° C. for approximately 12 hours, then allowed to cool to room temperature. A solution of 8.4 g $NaHCO_3$ in 700 mL water was added and the mixture was cooled to 0-5° C. The resulting precipitate was filtered and washed twice with cold water. The filter cake was dried, producing 14.59 g NOC (70.6% yield), and its liquid chromatography-measured purity at 210 nm was 92.59%.

Example 6: NME O-demethylation with PrSH/NaOt-Bu

A reaction vessel was carefully purged of nitrogen, with three 60 Torr vacuum-Nitrogen purges. The reaction vessel was thereafter carefully preserved from exposure to the atmosphere. 6.82 g sodium tert-butoxide (71.0 mmol) was dissolved in 45 mL DMF with stirring, producing a purple solution. 6.7 mL 1-propanethiol (74.3 mmol) were added via syringe. To this mixture was added a solution of 14.45 g NME (33.79 mmol) in 120 mL warm DMF, followed by a 12 mL DMF rinse. The reaction mixture was heated to 120° C. and refluxed at 115-125° C. for approximately 12 hours, then allowed to cool to room temperature. The mixture was then heated to 80° C. and a solution of 5.96 g $NaHCO_3$ in 354 mL water was added dropwise over one hour as the temperature was maintained at 75-85° C. The mixture was then cooled to 0-5° C. over two hours. The resulting precipitate was filtered and twice washed with 100 mL cold water. Upon vacuum drying at 80° C., 11.85 g of NOC was obtained (85.8% yield), and its liquid chromatography-measured purity at 210 nm was 95.00%.

Example 7: Preparation of Pure Nor-Buprenorphine 10.21 g crude norbuprenorphine base (24.69 mmol) and 3.78 grams L(+)-tartaric acid (25.18 mmol) were dissolved in 219 ml IPA and brought to 70 to 75° C. A small amount of the solution was withdrawn and scratched for seed crystal, then returned to the flask. When cloudiness was seen and crystal formation had begun, the mixture was cooled to 50 to 55° C. over a two hour period, then held in that temperature range for one hour longer. The slurry was filtered and the wet cake was washed with 30 ml IPA, then dried in a 60° C. vacuum oven. The bitartrate salt weighed 12.40 grams (89.1% yield).

10.89 g of the above bitartrate salt (19.32 mmol) was added to 511 ml of water and brought to 45 to 55° C. The pH was adjusted to 9.0 to 9.5 by the addition of 2M sodium hydroxide solution. The temperature was increased to 65 to 75° C. The solution became thick with precipitate but thinned out after 20 minutes of stirring. A few drops of 2M NaOH were added to return the pH, which had fallen to 8.97, back into the range 9.0 to 9.5. The solution was filtered hot and washed with approximately 50 ml of water. The wet cake was dried in an 80° C. vacuum oven to give 7.64 grams of pure norbuprenorphine base (96.7% recovery). Overall yield for this step was 86.2%.

Example 8: Preparation of NME 44.16 g N,O-Dimethylnorbuprenorphine (100 mmol), 6.22 g freshly powdered potassium carbonate (45 mmol), and 13.66 g cyanogen bromide were added to 101 mL dichloromethane. The slurry was placed under nitrogen and stirred and heated to reflux for ten hours, then stirred without heat for 12 hours. The mixture was cooled to 0-5° C., then 7.4 mL concentrated ammonium hydroxide was added. The solution was stirred for two hours at 0-10° C., then 54 mL of water was added and the mixture was stirred for ten minutes longer, then left to rest for at least 30 minutes. The layers were separated. The upper aqueous layer was extracted with 17 mL dichloromethane. The combined organic layers were extracted with a solution prepared from 1.3 mL concentrated ammonium hydroxide, 49 mL water, and 10 mL 20% aqueous sodium chloride. The organic layer was then extracted twice more, each time with a solution prepared from 49 mL water and 10 mL 20% aqueous sodium chloride. The yellow organic layer containing CMB weight 192.0 grams.

192.0 grams of the above CMB solution was added to 226 mL diethylene glycol and placed under nitrogen. The solution was slowly warmed to a temperature of 120° C. while dichloromethane distilled out. The solution was held at 120° C. for 30 minutes longer, then cooled to 85° C. 48 g sodium hydroxide solution (50%, 600 mmol) was then added slowly, allowing the temperature to rise to 100° C. The temperature was brought to 115 to 125° C. and held for ten hours, then cooled to 100° C. 453 mL water was then added dropwise while maintaining the temperature at 90-100° C. The solution was then cooled over a three-hour period to 0-5° C. The slurry was filtered and the NME product was dried in a 60° C. vacuum oven. The yield was 40.32 g (93% yield from N,O-dimethylnorbuprenorphine), approximately 98% pure.

Example 9: NME O-demethylation with 1-propanethiol/NaO$^t$Bu

A flange flask was set up and purged with nitrogen. Sodium tert-butoxide (4.7 g, 0.05 moles) and dimethylformamide (DMF) (31.0 mL, 0.4 moles) were charged to the flask and stirred for 5 minutes. No change in colour was observed. 1-Propanethiol (5.0 mL, 0.06 moles) was charged. A white precipitate was produced and a slight exotherm was observed. The mixture was stirred for 20 minutes.

Meanwhile, a solution of NME (10.0 g, 0.02 moles) in DMF (83.0 mL, 1.07 moles) was prepared. The solution was gently heated to dissolve the solid. After 20 minutes, the NME solution was charged to the sodium propanthiolate solution followed by a DMF rinse (8.0 mL, 0.1 moles). Whilst stirring, the temperature was increased to 115-125° C. over a period of 30 minutes and held at this temperature range with stirring for 20 hours.

After 20 hours, the reaction mixture was cooled to 80° C. and a solution of sodium bicarbonate (4.1 g, 0.05 moles) in water (245 mL, 13.6 moles) was added dropwise over a period of 2 hours. The mixture was then cooled to 0-5° C. and the resulting precipitate filtered, washed with water (2×200 mL) and dried overnight to produce 7.29 g of norbuprenorphine (75.1% yield) having a purity of 94.03% by area as determined by HPLC (λ=288 nm).

Example 10: NME O-demethylation with 1-dodecanethiol/KO$^t$Bu

Potassium tert-butoxide (5.9 g, 0.05 moles) was charged to a flange flask and the flask purged with nitrogen. DMF (105.0 mL, 1.36 moles) was charged and the mixture stirred until the solid had dissolved. 1-Dodecanethiol (12.6 mL, 0.05 moles) was added and a white precipitate was formed. NME (15.0 g, 0.035 moles) was charged and washed in with DMF (15.0 mL, 0.19 moles). The mixture was heated to 115-125° C. The mixture was cooled to 90° C. after 2.25 hours heating. A solution of sodium bicarbonate (6.18 g, 0.07 moles) in water (240 mL, 13.3 moles) was added dropwise to the mixture whilst maintaining the temperature at 85-95° C. The mixture was then cooled to <5° C., filtered, washed with water (2×200 mL), dried, treated with heptane and dried to produce 12.383 g of norbuprenorphine (85.3% yield) having a purity of 93.8% by area as determined by HPLC (λ=288 nm).

Example 11: Alternative O-demethylating Reagents

Based on the procedure of Example 10, experiments were carried out to assess the 3-O-demethylation of NME with various demethylation reagents. The reactions were carried out at approximately 120° C. unless otherwise specified and monitored by HPLC. The conditions were not optimized and serve to illustrate only that the reaction may be performed with the reagents listed.

| Base | Thiol | Conversion (% area by HPLC) |
|---|---|---|
| Sodium t-butoxide | Methyl 3-mercaptopropionate | 96.0% norbuprenorphine after 42 hours (at 150° C.) |
| Sodium t-butoxide | Propanethiol | 82.0% norbuprenorphine after 19.8 hours |
| Potassium t-butoxide | Propanethiol | 86.3% norbuprenorphine after 18.5 hours |

Example 12: Alternative Bases

Based on the procedure of Example 10, experiments were carried out to assess the 3-O-demethylation of NME with various bases. The reactions were carried out at approximately 120° C. unless other specified and monitored by HPLC. The conditions were not optimized and serve to illustrate only that the reaction may be performed with the reagents listed.

| Base | Thiol | Conversion (% area by HPLC) |
|---|---|---|
| Sodium t-butoxide | Propanethiol | 82.0% norbuprenorphine after 19.8 hours |
| Sodium ethoxide | Propanethiol | 59.36% norbuprenorphine after 20 hours |
| Sodium hydroxide | Propanethiol | 63.94% norbuprenorphine after 20 hours |
| NaH | 1-Dodecanethiol | 87.05% norbuprenorphine after 10.5 hours |
| n-BuLi | 1-Dodecanethiol | 45.88% norbuprenorphine after 9.5 hours |

-continued

| Base | Thiol | Conversion (% area by HPLC) |
|---|---|---|
| NaNH$_2$ | 1-Dodecanethiol | 58.09% norbuprenorphine after 20 hours |
| Triethylamine (comparative) | 1-Dodecanethiol | 0.17% norbuprenorphine after 4.5 hours |

The results in the table above demonstrate that alkoxides (such as sodium butoxide or ethoxide), hydrides, organolithium reagents (such as n-butyllithium) and amides (such as sodium amide) can be used in the processes of the present invention.

Triethylamine was also assessed but only a very low level of product was detected (0.17%). This is considered to be as a result of the similarity in pKa estimated for alkyl thiols and the conjugate acid of triethylamine.

Example 13: Alternative Solvent

The procedure of Example 10 was repeated using N-methyl-2-pyrrolidone (NMP) as the solvent, sodium t-butoxide and propanethiol to give norbuprenorphine (88.71% by area conversion by HPLC) after 18.5 hours reaction time.

Example 14: 0-Demethylation of N-cyano-3-O-methyl-norbuprenorphine

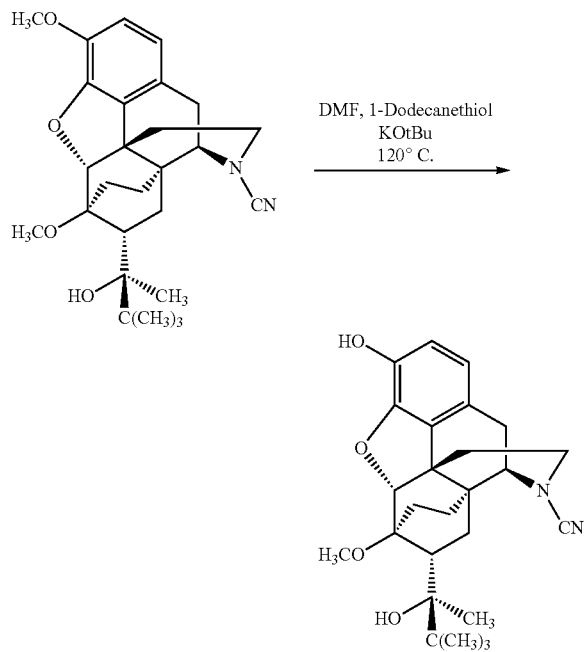

Following the procedure of Example 10, N-cyano-3-O-methyl-norbuprenorphine was 3-O-demethylated to N-cyano-norbuprenorphine after two hours (77.57% area conversion). LCMS analysis confirmed that the target product has formed. No norbuprenorphine was detected i.e. no cleavage of the cyano group occurred under the reaction conditions.

Example 15: Attempted O-demethylation of 3-O-methylbuprenorphine (Comparative)

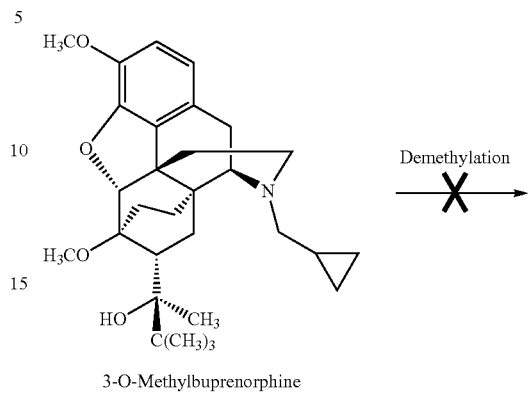

3-O-Methylbuprenorphine

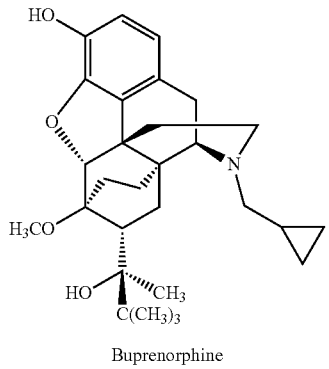

Buprenorphine

Potassium tert-butoxide (1.75 g, 15.60 mmoles) was charged to a flask round bottomed flask fitted with an overhead stirrer, condenser, temperature probe and nitrogen bubbler. The flask was purged with nitrogen. DMF (40 mL) was charged to the flask and the mixture was stirred. A sharp solution was formed. 1-Dodecanethiol (3.7 mL, 15.56 mmoles) was added and a thick, white precipitate was formed, which was allowed to stir out for 30 minutes. 3-O-Methylbuprenorphine (5.00 g, 10.38 mmoles) was added to the slurry and the reaction mixture heated to 120° C. The reaction mixture was heated at this temperature for 3 hours 15 minutes. After this time, the reaction mixture was analysed by HPLC. HPLC analysis indicated that 94.4% starting material remained and only 2.1% buprenorphine had been produced.

The demethylation was then attempted using sodium propanethiolate to determine if there were steric interactions preventing the long chain thiolate from participating in the demethylation reaction. However, this reaction was also unsuccessful and no product was detected.

Example 16: Attempted O-Demethylation of Other Morphinans (Comparative)

Using the procedure as described in Example 10, the O-demethylations of thebaine, hydrocodone and oxycodone were attempted:

| Starting Material | Target Product | Sample Point | Target Product (% area by HPLC) |
|---|---|---|---|
| Thebaine | Oripavine | 4 hours<br>21 hours | 20.79%<br>1.63% |
| Hydrocodone | Hydromorphone | 4 hours<br>21 hours | 2.35%<br>8.61% |
| Oxycodone | Oxymorphone | 4 hours<br>21 hours | 3.92%<br>0.49% |

Although some oripavine was formed from thebaine, the reaction was inefficient and an extended reaction time resulted in decomposition or further reaction of the product. As such, opiates containing the diene functionality do not appear to be stable to the demethylation reaction conditions.

Similar results were observed with hydrocodone or oxycodone as the starting material where it appears that the ketone functionality is not stable to the demethylation reaction conditions.

Example 17: O-Demethylation of Protected Oxycodone

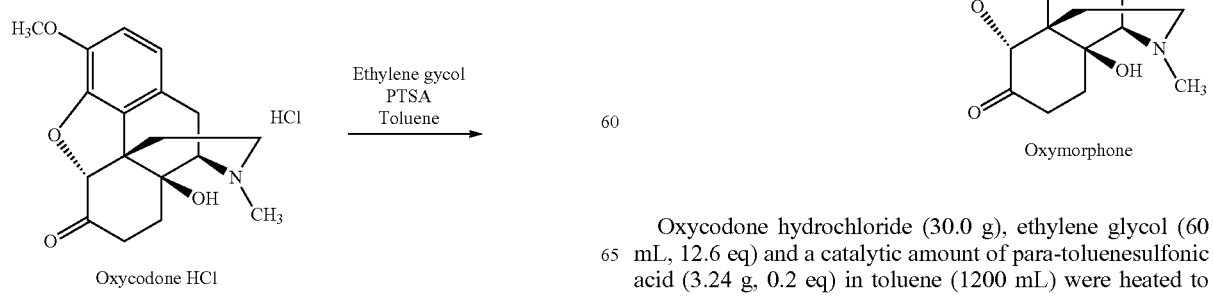

Oxycodone hydrochloride (30.0 g), ethylene glycol (60 mL, 12.6 eq) and a catalytic amount of para-toluenesulfonic acid (3.24 g, 0.2 eq) in toluene (1200 mL) were heated to reflux with the azeotropic removal of water. The reaction was heated over approx. 30 mins to 110° C. and a clear colourless solution was obtained. The reaction mixture was allowed to cool to room temperature and the pH adjusted from pH 6 to pH 9 with 0.88 ammonia solution (7.6 mL). The product was extracted into chloroform, washed with brine and dried over sodium sulfate. The solvent was removed and the product treated with methanol. After removal of the methanol, the white powder was dried to give oxycodone ketal (27.91 g).

Potassium tert-butoxide (18.73 g, 3 eq) was charged to a flange flask fitted with an overhead stirrer, condenser, temperature probe and nitrogen bubbler. The flask was purged with nitrogen. DMF (140 mL) was charged to the flask and the mixture was stirred. 1-Dodecanethiol (40 mL, 3 eq) was added and a thick, white precipitate was formed immediately. Oxycodone ketal (20.0 g) was added to the slurry and washed in with 20 mL DMF. The reaction mixture was heated to 120° C. and was heated at this temperature for approximately 8.25 hours. After this time, the reaction mixture was analysed by HPLC ($\lambda$=245 nm) and the results showed oxymorphone ketal (70.28% area) and oxymorphone (24.28% area) has formed.

All of the patents, published patent applications, journal articles, and other references cited in the present disclosure are incorporated by reference herein in their entireties for all useful purposes.

What is claimed:

1. A process for the preparation of a compound of formula (Ib),

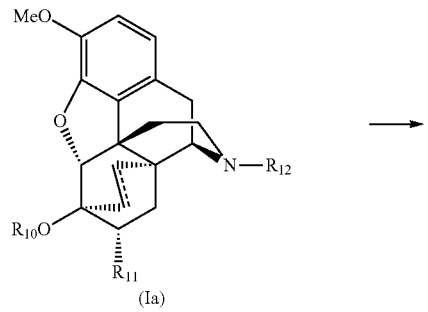

(Ia)

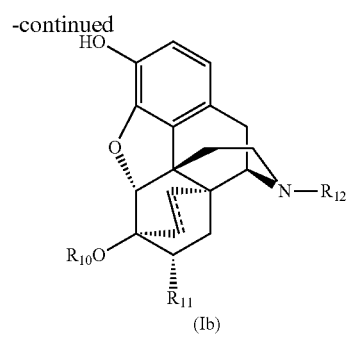

(Ib)

wherein:
$R_{10}$ is a straight-chain, branched or cyclic $C_1$-$C_{20}$ alkyl;
$R_{11}$ is $C(R_{13})(R_{14})(OH)$ or a protected $C(=O)(R_{15})$;
$R_{12}$ is H or CN;
$R_{13}$ is a straight-chain, branched or cyclic $C_1$-$C_{20}$-alkyl;
$R_{14}$ is a straight-chain, branched or cyclic $C_1$-$C_{20}$-alkyl; and
$R_{15}$ is a straight-chain, branched or cyclic $C_1$-$C_{20}$-alkyl
--- is a double bond or a single bond;
the process comprising:
i. reacting a compound of formula (Ia) with a thiolate in a suitable polar aprotic solvent, wherein the thiolate is selected from the group consisting of an optionally substituted $C_1$-$C_{20}$-alkylthiolate, an optionally substituted $C_6$-$C_{20}$-arylthiolate or an optionally substituted $C_7$-$C_{30}$-arylalkylthiolate; and
ii. treating the reaction mixture of step (i) with a protonating agent to give the compound of formula (Ib).

2. A process according to claim 1, wherein the thiolate is a $C_{10}$-$C_{20}$-alkylthiolate.

3. A process according to claim 2, wherein the $C_{10}$-$C_{20}$-alkylthiolate is a dodecanethiolate salt.

4. A process according to claim 1, wherein the thiolate is prepared from a thiol and a base which is capable of deprotonating the thiol.

5. A process according to claim 4, wherein the base is selected from the group consisting of alkali metal alkoxides, alkali metal hydroxides, alkali metal hydrides, organolithium reagents and alkali metal amides.

6. A process according to claim 1, wherein the polar aprotic solvent is selected from the group consisting of dimethylformamide, dimethylacetamide, N-methyl-2-pyrrolidone, dimethylsulfoxide, sulfolane, hexamethylphosphoramide and combinations thereof.

7. A process according to claim 1, wherein the reaction of step (i) may be conducted at a temperature in the range of about 100° C. to about 130° C.

* * * * *